(12) United States Patent
Rustum et al.

(10) Patent No.: US 6,939,893 B2
(45) Date of Patent: Sep. 6, 2005

(54) METHOD OF REDUCING TOXICITY OF ANTICANCER AGENTS

(75) Inventors: Youcef M. Rustum, Amherst, NY (US); Shousong Cao, East Amherst, NY (US); Farukh Durrani, Snyder, NY (US)

(73) Assignee: Health Research, Inc., Buffalo, NY (US)

( * ) Notice: Subject to any disclaimer, the term of this patent is extended or adjusted under 35 U.S.C. 154(b) by 25 days.

(21) Appl. No.: 10/315,721

(22) Filed: Dec. 10, 2002

(65) Prior Publication Data

US 2004/0110838 A1 Jun. 10, 2004

(51) Int. Cl.[7] ............... A61K 31/195; A61K 31/44; A61K 31/335; A66K 33/04
(52) U.S. Cl. ............... 514/561; 514/283; 514/449; 514/274; 424/702
(58) Field of Search ............... 424/649, 702; 514/274, 449, 283, 561

(56) References Cited

U.S. PATENT DOCUMENTS 4,617,189 A * 10/1986 Stockel et al. ............... 424/702
5,552,440 A * 9/1996 Crooks et al. ............... 514/553
6,197,295 B1 * 3/2001 Hsia et al. ............... 424/93.51

OTHER PUBLICATIONS

Vadgama J et al, Anticancer Res 20:1391–1414, 2000.*
Chen D et al, J Trace Elements in Exper Med 10:163–171, 1997.*
MEDLINE AN 96356155, Boucher et al, Nutrition, Sep.–Oct. 1995, 11 (5 Suppl), 708–11, abstract.*
CAPLUS 134:146813, Sieja, Pharmazie, 2000, 55(12), 958–959, abstract.*
EMBASE 2001377446, Frenkel, Current Pharmaceutical Design, 2001, 7/16, 1595–1614, abstract.*
Dong et al., *Identification of Molecular Targets Associated with Selenium–Induced Growth Inhibition in Human Breast Cells Uing cDNA Microarrays*, Cancer Research, Feb. 1, 2002, vol. 62, pp. 708–714.

El–Bayoumy et al., *The Protective Role of Selenium on Genetic Damage and on Cancer*, Mutation Research, 2001, vol. 475, pp. 123–129.
Hu et al., *The Protective Role of Selenium on the Toxicity of Cisplatin–Contained Chemotherapy Regimen in Cancer Patients*, Biological Trace Element Research, 1997, vol. 56, pp. 331–341.
Kajander et al., *Effects of Selenomethionine Metabolism in Cultured Malignant Cells*, Biochem. J., 1990, vol. 267, pp. 767–774.
Ohkawa et al., *The Effects of Co–Administration of Selenium and Cis–platin (CDDP) on CDDP–Induced Toxicity and Antitumor Activity*, Br. J. Cancer, 1988, vol. 58, pp. 34–41.
Seo et al., *Selenomethionine Regulation of p53 by a Refl–Dependent Redox Mechanism*, PNAS, Oct. 29, 2002, vol. 99, No. 22, pp. 14548–14553.
Wang et al., *Induction of Caspase–Mediated Apoptosis and Cell–Cycle $G_1$ Arrest by Selenium Metabolite Methylselenol*, Molecular Carcinogenesis, 2002, vol. 34, pp. 113–120.
Konorev et al., *Cell–Permeable Superoxide Dismutase and Glutahione Peroxidase Mimetics Afford Superior Protection Against Doxorubicin–Induced Cardiotoxicity: The Role of Reactive Oxygen and Nitrogen Intermediates*, Archives Biochem. Biophysics, 1999, 368 (2) pp. 421–428, abstract.
Korbac et al., *Doxorubicin Toxicity to the Skin: Possibility of Protection with Antioxidants Enriched Yeast*, J. Dermat. Sci., 2001, 25 (1) pp. 45–52, abstract.
Chen et al., *Protective Effects of Selenium Supplementation in Minimizing 5–Glorouracil Induced Lipid Peroxidative Damage of the Small Intestine*, J. Trace Elements in Experimental Med., 1997, 10 (3) pp. 163–171, abstract.

* cited by examiner

*Primary Examiner*—Rebecca Cook
(74) *Attorney, Agent, or Firm*—Hodgson Russ LLP

(57) ABSTRACT

The present invention discloses a method for enhancing the efficacy of anti-cancer agents. The method comprises administering to an individual, in need of such a treatment, an anti-cancer agent and a selenium compound. The selenium compounds may be administered before, during or after administration of the anti-cancer agent.

12 Claims, 4 Drawing Sheets

METHOD OF REDUCING TOXICITY OF ANTICANCER AGENTS

FIELD OF THE INVENTION

This invention relates generally to the field of cancer therapy and more particularly to a method for reducing undesirable toxicity of chemotherapeutic agents.

DESCRIPTION OF RELATED ART

Chemotherapy is now a recognized and widely used modality of cancer treatment. Depending upon the type of cancer, chemotherapy is often the primary course of treatment. For example, chemotherapy is widely used either alone or in combination with other treatments such as radiation treatment for a variety of cancers including cancer of the ovary, testis, breast, bladder, colon, head and neck as well as leukemia, lymphomas, sarcomas, melanomas, myelomas and others.

Chemotherapeutic agents are broadly classified into a number of groups. The majority of anticancer drugs act as cytotoxic drugs. The classification of these drugs into groups is mechanism based. While chemotherapeutic agents have proven extremely useful in the treatment of cancer, nearly all of them are associated with significant toxic effects because of their potential to kill cancerous as well as healthy cells. The toxicity associated with anticancer drugs often forces discontinuation of treatment which may negatively impact the prognosis of patient's condition and clinical outcome and result in compromising the quality of life.

Some recent studies have attempted to address the issue of toxicity of anticancer agents (Steifel et al., 1999, WO 99/64018; Chen et al., 1986, J. Nurtition, 116(12): 2453–2465; Dobric et al., 1998, J. Environ. Pathol. Toxicol Oncol., 17:291–299. However, these studies only describe the effects of selenium on in vitro toxicity of certain anti-cancer agents. Given the inherent difficulties of extrapolating the in vitro studies to treatment regimens for cancer patients, it is not clear whether the in vivo toxicity of anticancer agents can be reduced. Some in vivo studies (Van Vleet et al., 1980, Am. J. Pathol., 99:13–42; Van Vleet et al., Am. J. Vet Res., 1980, 41(5):691–699; Van Vleet et al., Am. J. Vet Res., 1981, 42(7):1153–1159 indicate that selenium failed to alter the in vivo toxicity induced by adriamycin. Accordingly, currently there is no effective way to reduce the toxicity of anticancer agents without compromising their efficacy. Thus there is a need in the field of cancer chemotherapy to identify methods and compositions by which the toxic side effects can be reduced without compromising the anticancer efficacy.

SUMMARY OF THE INVENTION

In the present invention it was observed that administration of selenium compounds reduces the toxicity of anticancer agents. Data is presented for in vivo studies in two animal models.

The present invention discloses a method for reducing the toxicity of anticancer agents. The method comprises administering to an individual, in need of treatment, an anti-tumor agent and a selenium compound. The selenium compounds may be administered before, during or after administration of the anti-cancer agent. In one embodiment, the selenium compound is administered prior to chemotherapy and may be continued during and after the chemotherapy.

DETAILED DESCRIPTION OF THE INVENTION

Figure 1:
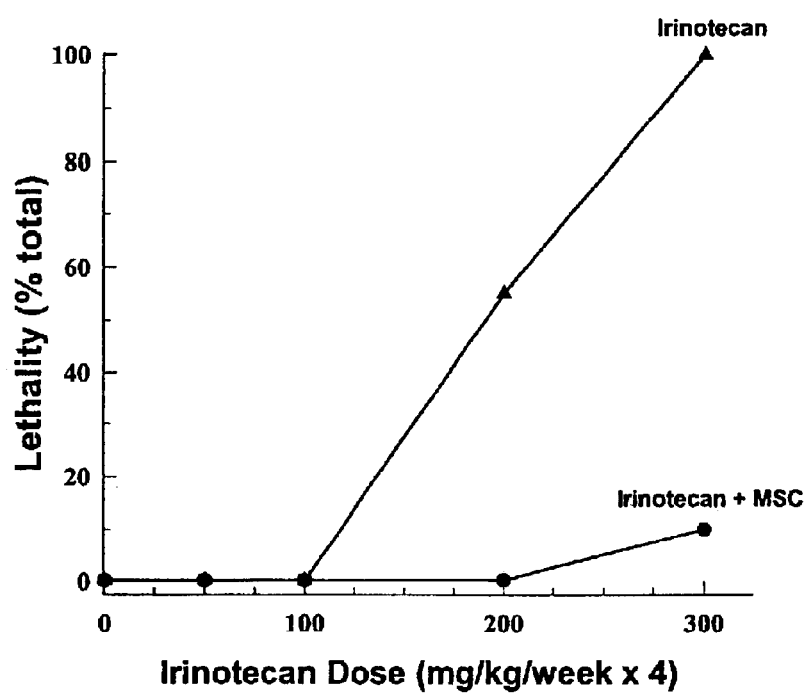
FIG. 1 is a representation of the effect of selenium on the toxicity of irinotecan (CPT-11) in nude mice. Irinotecan was administered by i.v. push once a week for 4 weeks and methylselenocysteine (MSC) by oral route (p.o.) daily for 42 days with the first dose administered 21 days prior to the administration of irinotecan. The data are combined from at least three independent experiments with five (5) animals per experiment.

The term "therapeutic dose" as used herein means the dosage of a therapeutic agent that is acceptable for use clinically with respect to its toxicity without the co-administration of selenium compounds.

The present invention discloses a method for reducing the toxicity of anticancer agents while maintaining or enhancing their efficacy. The method comprises administering to an individual, in need of such a treatment, one or more anti-cancer agents and one or more selenium compounds. The selenium compounds may be administered before, during or after administration of the anticancer agent. By combining chemotherapy with the administration of selenium compounds, the toxicity of the chemotherapeutic agent can be decreased.

This invention is useful for reducing the toxicity of anticancer agents including fluoropyrimidines, pyrimidine nucleosides, purines, platinum analogues, antroacyclines, podophyllotoxins, camptothecins, hormones and hormone analogues, enzymes, proteins and antibodies, vinca alkaloids, taxanes. The anti-cancer agents for the present invention generally fall into one or more of the following functional categories: antihormones, antifolates, antimicrotubule agents, alkylating agents, antimetabolites, antibiotics, topoisomerase inhibitors and antivirals.

Selenium compounds useful for the present invention can be from either organic or inorganic forms. It is preferable to use selenium from organic forms since these are known to be less toxic. Examples of useful selenium compounds from organic forms include methylselenocysteine (MSC) and seleno-L-methionine (SLM). The doses of selenium compounds are in the range of about 200 $\mu$g/person to about 3.6 mg/person and maybe administered daily for 1 year or longer. It has been reported that up to 800 $\mu$g/patient is generally considered to be safe without associated toxicity.

The present invention comprises the steps of combining chemotherapy with the administration of selenium. One or more chemotherapeutic agents may be used accordingly to the criteria well known in the art of cancer chemotherapeutics. The dosage and administrative regimens of the chemotherapeutics are well within the purview of those skilled in the art. Selenium administration can be initiated before the start of chemotherapy, during chemotherapy or after cessation of chemotherapy. If initiated before the start of chemotherapy, selenium administration can be continued during the chemotherapy and after cessation of chemotherapy. Similarly, if initiated during chemotherapy, selenium administration can continue after cessation of chemotherapy.

While the present method for reducing toxicity is applicable for any chemotherapeutic agent some exemplary ones are irinotecan, FU, taxol, cisplatin adriamycin, oxaliplatin, cyclophasphamide, and EGF and VGF inhibitors. In addition, the present invention can also be used for reducing the toxicity associated with other anticancer therapies such as radiation treatment.

To demonstrate the effect of selenium in reducing the toxic effect of chemotherapeutic agents, two animal models were used. Thus, studies were carried out in normal nude mice and rats as well as in tumor bearing nude mice. It should be noted that while previous studies have reported an effect of selenium on reducing toxicity (such as cardiotoxicity) of some anticancer agents in vitro, there has been no demonstration of an effect of selenium on the in vivo toxicity of these agents. Further, the in vitro studies also do not permit an assessment of the effect of selenium on the efficacy of anticancer agents.

In one embodiment of the invention, it was determined that methylselenocysteine (MSC) and seleno-L-methionine (SLM) are effective agents in protecting from toxic and lethal doses of four classes of clinically approved chemotherapeutic agents; namely irinotecan (topoisomere I inhibitor); FU (DNA synthetic inhibitor); taxol (microtubule inhibitor) and cisplatin (DNA alkalating agent). The two selenium containing compounds were evaluated in two host systems (mice and rats) against agents representing four classes of anticancer drugs. The in vivo effects were observed using non-toxic doses of the selenium containing compounds (about 0.2 mg/mouse/day or lower).

When selenium is administered to an individual in need of therapy for cancer to reduce the toxicity, the dose of the chemotherapeutic agent (or radiation dose) can be increased so as to have greater efficacy.

The following examples are provided below to illustrate the present invention. These examples are intended to be illustrative and are not to be construed as limiting in any way.

EXAMPLE 1

Evaluation of the effects of selenium on the in vivo toxicity of irinotecan in normal nude mice. This embodiment demonstrates that selenium reduces toxocity induced by irinotecan. To illustrate this embodiment, nude mice were administered 42 single, daily oral doses of 0.2 mg/mouse of MSC. After 21 days, irinotecan was administered intravenously in doses of 50, 100, 200 and 300 mg/kg/wk×4. The data in FIG. 1 is a summary of the results from at least three separate experiments with five (5) mice per group obtained with irinotecan alone and in combination with the 42 daily oral administrations of MSC.

The results can be summarized as follows: Amongst the concentration studies, the maximum tolerated dose (MTD) of 100 mg/kg/wk irinotecan resulted in less than 20% weight loss and no lethality (100% of animal survived treatment). The addition of MSC to this regimen results in decrease in overall body weight loss, signifying improved animal well being. With the MSC treatment of this group, the weight loss was less than what was observed with irinotecan alone. In contrast with 200 mg/kg/wk×4 doses and 300 mg/kg/wk×4 of irinotecan representing twice and three times the MTD's, MSC provided 100% and 80% protection, respectively. Thus, with 200 mg/kg/wk×4 doses of irinotecan, 55% of animals died by the end of treatment while none of the animals died (100% survived) when treated with MSC. These data demonstrate that selenium protects against lethal doses of irinotecan.

EXAMPLE 2

Evaluation of the effects of MSC on the toxicity of irinotecan (CPT-11) in normal rats. To demonstrate the effects of MSC on irinotecan induced toxicity in another species, rats were administered orally with 1 mg/kg/rat daily for 18 days with the first dose administered 14 days prior to irinotecan treatment. In the treated group, irinotecan was administered by i.v. push once a day for three (3) days. The results are shown in FIG. 2.

Figure 2:
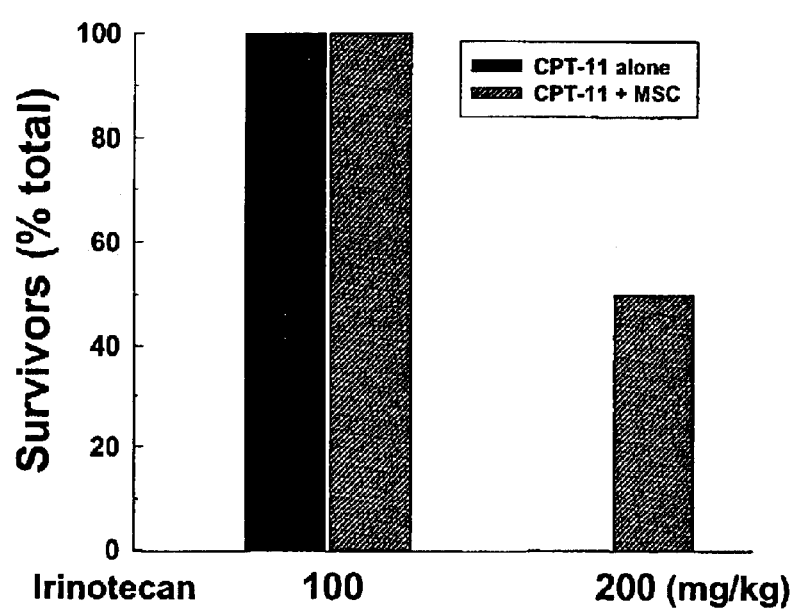
FIG. 2 is a representation of the effect of selenium compounds on the toxicity of irinotecan in rats. Irinotecan was administered by intravenous (i.v.) push once for three (3) days and MSC by p.o. at 1 mg/kg/rat daily for 18 days with the first dose being given at 14 days before irinotecan treatment. The data are combined from 2–5 independent experiments with four (4) animals for each experiment.

The data in FIG. 2 is a summary of the survival results obtained in two experiments using four (4) rats per group demonstrating the protective effects of MSC. A protective effect of MSC was observed when the concentration of irinotecan was increased to 200 mg/kg/day for three (3) days (twice the MTD), wherein all the animals in the group administered irinotecan alone died, only 50% of the animals died in the group administered MSC plus irinotecan.

EXAMPLE 3

Evaluation of the effects of MSC on the toxicity of irinotecan in tumor bearing animals. To demonstrate the effect of MSC on the antitumor activity of chemotherapy, nude mice bearing transplantable squamous cell carcinoma of the head and neck (A253) were transplanted subcutaneously (s.c.) with tumor fragments and drug treatments were initiated when tumor sizes approach about 200 mg in size. Irinotecan was administered at 100 times maximum tolerated dose (MTD), 200 or 300 mg/kg/wk for four (4) weeks representing two (2) and three (3) times the MTD, respectively in the presence or absence of MSC 0.2 mg/mouse/day. MSC was administered for 42 days and irinotecan was administered after the first 21 days of the MSC treatment. The results are presented in Table 1.

TABLE 1

Antitumor Activity of Irinotecan by Methylselenocysteine (MSC) in Xenographts Bearing Transplantable Sequamous Cell Carcinoma of the head and neck (A253)

| Treatment* | Response Rate (%) | | Survivors (%) |
| --- | --- | --- | --- |
| | PR | CR | |
| Irinotecan (100) | 20 | 20 | 100 |
| Irinotecan (100) + MSC | 40 | 60 | 100 |
| Irinotecan (200) | NA† | NA† | 45 |
| Irinotecan (200) + MSC | 20 | 80 | 100 |
| Irinotecan (300) | NA† | NA† | 0 |
| Irinotecan (300) + MSC | 20 | 80 | 80 |

*Irinotecan mg/kg/wk × 4 (i.v.); MSC, 0.2 mg/mouse/d × 42 (p.o.) with MSC administered for 21 days prior to treatment with Irinotecan.
†NA, response was not tabulated since death occurred in 65 to 100 of the animals during treatment. The surviving animals did not achieve CR.

The data in Table 1 represents a summary of the therapeutic selectivity of the combination of irinotecan with MSC. The data indicate that MSC protection against irinotecan induced toxicity was selective resulting in increased survivorsprotection) of animals treated with lethal doses of irinotecan (200 mg/kg). Under the condition of selective protection, the antitumor activity of irinotecan was significantly increased from 20% complete tumor response (CR) with irinotecan alone to 80% CR in combination with MSC.

EXAMPLE 4

Figure 3:
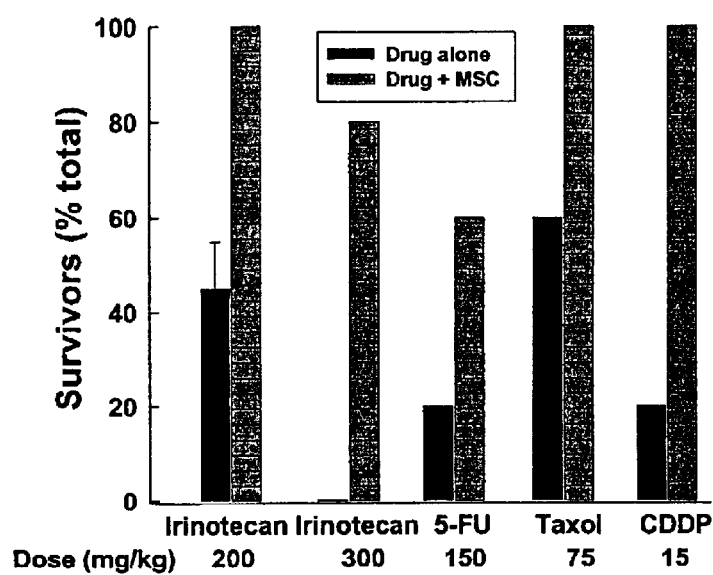
FIG. 3 is a representation of the effect of selenium on survival rate of nude mice upon administration of irinotecan. Data are presented for cisplatin (CDDP), taxol, 5-Fluorouracil (FU) and irinotecan with or without selenium treatment.

Evaluation of effects of selenium on the toxicity of Chemotherapeutic agents To demonstrate that the effect of selenium in reducing toxicity is not limited to irinotecan, the effects of selenium on toxicity induced by Taxol, FU, and cisplatin was evaluated in normal nude mice. Except for the weekly schedule of irinotecan, taxol (75 mg/kg), 5-FU (150 mg/kg) and cisplatin (15 mg/kg) were administered once via the intravenously route. In all cases drug doses used were toxic and above the maximum tolerated dose. The results are shown in FIG. 3. For each chemotherapeutic agent, a protective effect of MSC was observed on the survival rate of animals. Thus, these data indicate the general applicability of selenium as modulator of host toxicity induced by chemotherapeutic agents. It is important to note that chemotherapeutic agents used herein represent different classes of anticancer drugs, i.e., a topoisomerase I inhibitor (irinotecan); a DNA synthesized inhibitor (FU); a microtubule inhibitor (taxol); and a DNA alkalating agent (cisplatin).

EXAMPLE 5

Figure 4:
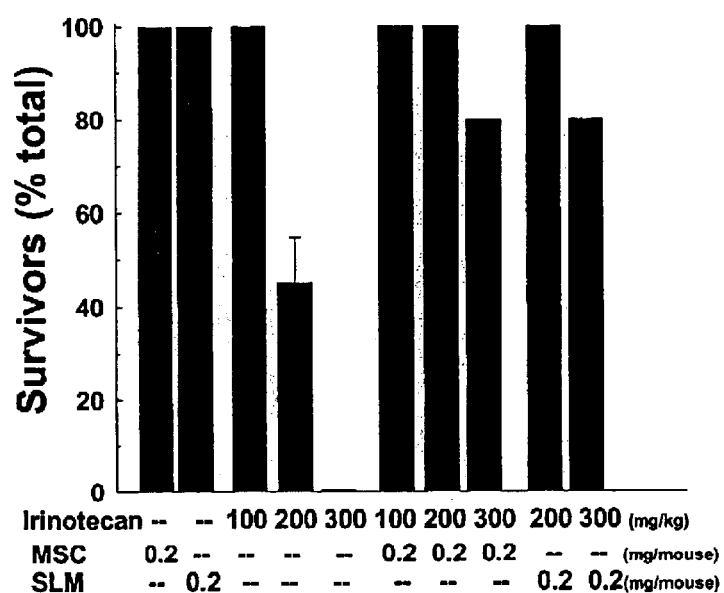
FIG. 4 is a representation of the effect of two selenium compounds on the survival rate in nude mice upon administration of irinotecan. Irinotecan was administered by i.v. push once a week for 4 weeks, MSC and seleno-L-methionine (SLM) were given p.o. daily for 28 days with the first dose being administered 7 days before irinotecan treatment. Five mice were used for each experiment group for irinotecan+MSC, four experiments were done with 100 mg/kg and 200 mg/kg, two experiments with 300 mg/kg, two experiments for irinotecan+SLM.

Comparative evaluation of MSC and SLM as modulators of toxicity induced by irinotecan in normal nude mice. To determine if selenium compounds other than MSC can also provide protective effects against toxicity induced by chemotherapeutic agents, a comparative study of MSC and SLM was carried out in nude mice. Irinotecan was administered by i.v. push once a week for 4 weeks. MSC and SLM were given p.o. daily for 28 days and the first dose was administered seven (7) days prior to irinotecan treatment. Each experimental group had 10 mice each from two (2) independent experiments. The results are shown in FIG. 4. Using a irinotecan dose of 200 mg/kg/wk×4, which produced approximately 55% lethality (45% survivors), MSC and SLM were equally effective in reducing toxicity. This data indicates the protective effects are not specific for MSC, but SLM produced similar results.

EXAMPLE 6

Role of MSC dose in modulating the toxicity of irinotecan. In order to identify the minimum dose of MSC in the successful modulation of drug induced toxicities. Studies were carried out in normal mice treated with different doses of MSC (0.01 to 0.2 mg/mouse/day×42) in combination with irinotecan (200 mg/kg/wk×4). The results indicate that an MSC dose as low as 0.01 mg/mouse was sufficient to offer complete protection against lethal doses of irinotecan with no lethality with the combination. In contrast, irinotecan alone yielded 50% lethality. Those skilled in the art will recognize that by conducting experiments as described herein, optimal doses of selenium for reducing toxicity of other chemotherapeutic agents and other anticancer modalities can be easily determined.

EXAMPLE 7

Effects of MSC on the hematologic toxicity induced by irinotecan in normal nude mice. With the rodent model used in this invention, the dose limiting toxicity associated with irinotecan in rats was diarrhea, mouth ulceration and hematologic toxicity, and in mice primarily hematologic toxicity. MSC was administered 0.2 mg/mouse/day with the first dose administered seven (7) days prior to irinotecan treatment. Twenty-four (24) hours after the third weekly dose of irinotecan blood samples were removed and analyzed for the parameters outlined in Table 2. All hematological parameters were determined by standard methods. As demonstrated in FIG. 2, MSC offered complete protection in 50% of animals with severe diarrhea at the 200 mg/kg dose of irinotecan. To identify possible mechanisms of action of the selenium compounds in reducing the hematologic toxicity induced by irinotecan, the effects of MSC with or without irinotecan were investigated on hematological parameters. The data in Table 2 indicates that over 60% reduction in white blood cells was observed in mice (9.4 to 3.5), i.e. significant neutropenia was induced by irinotecan at a 200 mg/kg/wk dose, a dose limiting toxicity similar to what is normally observed in patients treated with irinotecan. These data demonstrate that MSC can effectively prevent neutropenia toxicity induced by irinotecan. Irinotecan, either alone or in combination with MSC had no significant effect on the other hematologic parameters.

TABLE 2

Hematological changes of Irinotecan ± MSC in nude mice on day 22 after initial treatment of Irinotecan (24 h after third dose)

| Treatment | WBC | RBC | HGB | HCT |
|---|---|---|---|---|
| Control | 9.4 ± 3.6 | 8.7 ± 0.9 | 16.1 ± 1.6 | 46.1 ± 2.1 |
| MSC (0.2)* | 10.3 ± 4.5 | 9.1 ± 0.5 | 16.8 ± 0.7 | 49.4 ± 2.4 |
| Irinotecan (200)** | 3.5 ± 0.5 | 7.8 ± 1.0 | 13.8 ± 1.9 | 40.9 ± 4.2 |
| Irinotecan (200)** + MSC (0.2)* | 8.2 ± 3.1 | 8.5 ± 0.5 | 15.4 ± 0.7 | 44.8 ± 1.8 |

| Treatment | MCV | MCH | MCHC | PLT |
|---|---|---|---|---|
| Control | 53.4 ± 1.0 | 18.6 ± 0.1 | 34.5 ± 0.6 | 1118 ± 415 |
| MSC (0.2)* | 54.0 ± 1.0 | 18.4 ± 0.7 | 34.0 ± 0.7 | 756 ± 231 |
| Irinotecan (200)** | 52.8 ± 0.8 | 17.5 ± 0.3 | 32.7 ± 0.6 | 836 ± 201 |
| Irinotecan (200)** + MSC (0.2)* | 52.8 ± 1.5 | 18.0 ± 0.5 | 34.0 ± 0.6 | 1174 ± 152 |

*mg/mouse;
**mg/kg; three mice for each group with duplicate samples (6 samples).
WBC: white blood cell(THSN/CU MM);
RBC: red blood cell (Mill/CU MM);
HGB: hemoglobin (Gram/DL);
HCT: haematocrit (%);
MCV: mean corpuscular volume (CU Microns);
MCH: mean corpuscular hemoglobin (PICO Grams);
MCHC: mean corpuscular hemoglobin concentration (%);
PLT: platelets (THSN/CU MM).

The data presented herein demonstrate that non-toxic doses of selenium compounds protect mice against toxicity induced by irinotecan. As an example, it is demonstrated herein that MSC offers complete protection against hematologic toxicity induced by irinotecan (200 mg/kg/wk×4, a dose at which 55% of mice would normally die of toxicity. Complete protection from irinotecan induced toxicity was associated with complete protection against hematologic toxicity.

EXAMPLE 8

Reversal of renal toxicity induced by Cisplatin (CDDP). The dose limiting toxicity of therapeutic doses of cisplatin is kidney toxicity. Studies were performed to identify blood biological markers modified by CDDP and to evaluate the ability of MSC to reverse the process. Four groups of six animals each were used. The first group was untreated rats (control), the second group was given MSC at 0.75 mg/rat/day for 20 days and samples collected 2 hours after MSC administration on day 20. The third group was administered CDDP alone at 6 mg/kg by a single

TABLE 3

Renal function test after CDDP ± MSC treatment in rats

| Treatment | Blood Urea Nitrogen (mg/dl) | Creatinine (mg/dl) |
|---|---|---|
| Control | 16.0 ± 2.0* | 0.32 ± 0.04 |
| MSC (0.75) | 12.7 ± 1.2 | 0.30 ± 0.00 |
| CDDP (6) | 147.2 ± 103 | 2.78 ± 2.57 |
| CDDP (6) + MSC (0.75) | 32.7 ± 6.8 | 0.43 ± 0.05 |

*Mean ± SD.
CDDP (6 mg/kg) was administered by a single i.v. push and MSC (0.75 mg/rat) daily for 20 days which start 14 days before CDDP; the animals were sacrificed on days after CDDP treatment. Six rats for each group.

i.v. injection and samples were collected on day 6. The fourth group was adminstered MSC (0.75 mg/rat/day for 20 days) with CDDP (6 mg/kg). CDDP was given 14 days after MSC administration and NSC was given for 6 more days after CDDP administration. Samples were collected on day 6 after CDDP administration. Blood samples were collected at postmortem by cardiac puncture. Serum was obtained from the blood samples and urea nitrogen and creatinine concentrations were determined by standard methods using commercially kits (Ortho Clinical Diagnostics).

The data, shown in Table 3, indicates a dramatic upregulation of these markers induced by CDDP treatment and return the level of these markers to approximately control values when MSC was co-administered with CDDP. This indicates that MSC is highly effective in reversal of markers associated with kidney toxicity, namely blood urea nitrogen (BUN) and creatinine. Furthermore, morphological and structural modifications induced by CDDP in kidney were not detectable in kidneys of animals treated with MSC in combination with CDDP.

In summary, the data presented here indicate that severe toxicity experienced with administration of anticancer agents is reduced by administration of selenium compounds offering the potential of the use of selenium containing compounds as a modulator of the therapeutic selectivity and efficacy of broad spectrum and clinically active chemotherapeutic agents. The use of these agents as a modulator of toxicity and antitumor activity of broad spectrum of anticancer agent is unexpected. Thus, this approach will have a significant impact on quality of life and survival of cancer patients treated with chemotherapy.

What is claimed is:

1. A method for reducing the in vivo toxicity the anticancer agent irinotecan comprising the steps of administering to an individual in need of treatment for cancer a therapeutically effective dose of irinotecan, and a selenium compound in an amount effective to reduce toxicity of the anticancer agent wherein the toxicity induced by the irinotecan is less than the toxicity induced by the same amount of the irinotecan in the absence of the administered selenium compound.

2. The method of claim 1, wherein the selenium compound is seleno-L-methionine.

3. The method of claim 1, wherein the selenium compound is methylselenocysteine.

4. The method of claim 1, wherein the selenium compound is administered prior to administration of the anticancer agent, during administration of the anticancer agent and/or following administration of the anticancer agent.

5. A method for using an anticancer agent selected from the group consisting of taxol and irinotecan at a higher than therapeutic dose comprising the steps of administering to an individual in need of treatment for cancer a higher than therapeutic dose of the anticancer agent and a selenium compound in an amount effective to reduce toxicity of the anticancer agent, wherein the toxicity of the anticancer agent is reduced with the administration of the selenium compound.

6. The method of claim 5, wherein the anticancer agent is taxol.

7. The method of claim 5, wherein the anticancer agent is irinotecan.

8. The method of claim 5, wherein the selenium compound is seleno-L-methionine.

9. The method of claim 5, wherein the selenium compound is methylselenocysteine.

10. The method of claim 1, wherein the selenium compound is administered prior to administration of the anticancer agent, during administration of the anticancer agent and/or following administration of the anticancer agent.

11. The method of claim 4, wherein the administration of the selenium compound is initiated prior to administration of the anticancer agent.

12. The method of claim 10, wherein the administration of the selenium compound is initiated prior to administration of the anticancer agent.

* * * * *